US00PP13434P3

(12) United States Plant Patent
Cammarota

(10) Patent No.: US PP13,434 P3
(45) Date of Patent: Dec. 31, 2002

(54) PHLOX PLANT NAMED 'BUBBLE GUM'

(76) Inventor: Thomas Cammarota, 2541 City View St., Eugene, OR (US) 97405

( * ) Notice: Subject to any disclaimer, the term of this patent is extended or adjusted under 35 U.S.C. 154(b) by 0 days.

(21) Appl. No.: 09/801,205

(22) Filed: Mar. 7, 2001

(65) Prior Publication Data

US 2002/0129420 P1 Sep. 12, 2002

(51) Int. Cl.[7] ..... A01H 5/00
(52) U.S. Cl. ..... Plt./320

(58) Field of Search ..... Plt./320

*Primary Examiner*—Bruce R. Campell
*Assistant Examiner*—W C Haas
(74) *Attorney, Agent, or Firm*—Mark P. Bourgeois

(57) ABSTRACT

A new cultivar of Phlox plant named 'Bubble Gum' that is characterized by vigorous growth, prolific blooming, tall, erect and uniform habit and bright pink flowers, with dark markings at the center of each flower. In combination with these characteristics, the new cultivar is larger and not as rangy as other pink varieties, setting it apart from all other existing varieties of Phlox.

2 Drawing Sheets

BOTANICAL CLASSIFICATION

*Phlox subulata* 'Bubble Gum'.

CROSS-REFERENCES TO RELATED APPLICATIONS

The application for Phlox 'Bubble Gum' is related to another application entitled Phlox Plant Named 'Cotton Candy', U.S. patent application Ser. No. 09/800,866, having the same inventor and filing date as the present invention.

BACKGROUND OF THE INVENTION

The present invention relates to a new and distinct cultivar of Moss Phlox known botanically as *Phlox subulata* (not patented) and hereinafter referred to by the cultivar name 'Bubble Gum'. In 1998 the new cultivar was discovered by the inventor, in a cultivated area of Albany, Oreg. 'Bubble Gum' was a spontaneously occurring sport, discovered as a branch on *Phlox subulata* 'Candy Stripe' (not patented).

The distinguishing characteristics of 'Bubble Gum' include a tall, erect habit and floriferous display of bright pink flowers. 'Bubble Gum' is distinguished from the parent plant 'Candy Stripe' (prior art) by pink flowers. It differs from the pink variety 'Emerald Pink' (unpatented) by its large size and abundance of flowers, and is not disease prone or rangy in habit like the pink variety 'Rosea' (unpatented).

After the sport was observed for performance over a period of months, 'Bubble Gum' was propagated in a cultivated area of Albany, Oreg. The first asexual reproduction was accomplished by the inventor in 1998, using vegetative cuttings. The distinguishing characteristics have been determined stable and are reproduced true to type in successive generations.

SUMMARY OF THE INVENTION

The following traits have been repeatedly observed and represent the characteristics of the new cultivar. These attributes in combination distinguish this cultivar from other commercial varieties. 'Bubble gum' has not been tested under all possible conditions and phenotypic differences may be observed with variations in conditions, however without any variance in genotype.

1. 'Bubble Gum' is vigorous in growth.
2. 'Bubble Gum' is a prolific bloomer.
3. 'Bubble Gum' is tall and erect with a uniform habit.
4. 'Bubble Gum' has bright pink flowers with dark markings at the center encircling the opening to the throat.
5. 'Bubble Gum' is large in size, floriferous and not rangy in habit like other pink varieties.
6. 'Bubble Gum' is hardy to USDA Zone 3.

BRIEF DESCRIPTION OF THE DRAWINGS

The accompanying color photographs illustrate the distinguishing traits of the new cultivar.

The first drawing sheet shows a side view of the entire plant of the new cultivar 'Bubble Gum'.

The second drawing sheet is a close-up view of the mature flowers of 'Bubble Gum'. The photographs are made using conventional photographic techniques and although colors may appear different from actual colors due to light reflectance, they are as accurate as possible by conventional photography.

BOTANICAL DESCRIPTION OF THE PLANT

The following is a detailed botanical description of the new Phlox cultivar 'Bubble Gum'. Data was collected in Arroyo Grande, Calif. from 12 month old plants grown in two-gallon containers. The plants were grown outdoors with full sun in the morning and then partial shade in the afternoon. The plants were grown in loose well drained soil with a time release fertilizer and were moderately watered. The color determination is in accordance with The R.H.S. Colour Chart of The Royal Horticultural Society, London England, except where general color terms of ordinary dictionary significance are used. The growing requirements are similar to the species and no disease problems have been observed.

Botanical classification: *Phlox subulata* 'Bubble Gum'.
Common name: Moss Phlox.
Parentage: 'Bubble Gum' was a spontaneously occurring sport, discovered as a branch of the parent plant *Phlox subulata* 'Candy Stripe' (prior art).
Propagation: By soft stem cuttings or division.
Rooting habit: Vigorous, fibrous and well branched.
Time to initiate roots: Approximately 21 days at temperatures of 25 degrees Centigrade for roots to develop from an initial cutting.
Crop time: Approximately 24 to 36 weeks to produce a finished plant in a one gallon container, from an unrooted cutting.
Plant habit: Spreading habit.
Use: Used as a groundcover, border plant and in rock gardens.
Type: Perennial.
Growth rate: Vigorous growth rate.
Height: Soil level to top of leaves is approximately 7 cm. in height and soil level to top of flowers is approximately 10 cm. in height.
Width: 40 cm. in width.
Hardiness: USDA Zone 3.
Stem:
*Stem color.*—138B overlaid with streaks of 183A.
*Stem shape.*—Cylindrical in shape.
*Internode length.*—6–18 mm. between nodes.
*Stem width.*—2 mm. in width.
*Stem length.*—7–8 cm. in length.
*Stem surface.*—Puberulent.
*Branching habit.*—Freely branching and dense.
Foliage:
*Leaf arrangement.*—Opposite.
*Leaf division.*—Simple.
*Leaf shape.*—Narrow and linear in shape.
*Leaf length.*—4–12 mm. in length.
*Leaf width.*—1–3 mm. in width.
*Leaf apex.*—Apiculate.
*Leaf base.*—Truncate.
*Leaf venation.*—Only mid-vein is visible and slightly depressed on adaxial surface, while slightly protruding on abaxial surface.
*Vein color.*—137A.
*Margin type.*—Entire with margins slightly involute.
*Leaf surface.*—Adaxial and abaxial surfaces generally glabrous with hairs toward margins and base.
*Petiole.*—Sessile attachment.
*Young leaf color* (*adaxial surface*).—137A.
*Young leaf color* (*abaxial surface*).—137B.
*Mature leaf color* (*adaxial surface*).—136A.
*Mature leaf color* (*abaxial surface*).—137A.
*Foliar fragrance.*—None observed.
Flower:
*Sexuality.*—Monoclinous.
*Flowering season.*—Early to mid spring. Plants may flower in summer as well.
*Flower arrangement.*—Generally three held upright and above foliage.
*Flower form.*—Corymb.
*Quantity of flowers.*—Six flowers per corymb.
*Flower shape.*—Explanate.
*Fragrance.*—Slight sweet perfume scent.
*Determinate or indeterminate.*—Determinate.
*Flowering time.*—Diurnal.
*Flower aspect.*—Outward aspect.
*Flower diameter.*—2 cm. in diameter.
*Flower depth* (*corolla tube*).—12 mm. in depth.
*Peduncle length.*—3–3.5 cm. in length.
*Peduncle width.*—1 mm. in width.
*Angle of peduncle to stem.*—45_angle to stem.
*Peduncle color*—86A.
*Petals.*—Five in number.
*Petal length.*—12 mm. in length.
*Petal width.*—9 mm. in width at widest part and 3 mm. in width at narrowest part.
*Fused or unfused.*—Unfused.
*Petal color* (*opening*).—78C.
*Petal color* (*mature*).—Overall color is 72C with dark markings 71A at the center of the flower encircling the opening to the throat.
*Petal shape.*—Obovate with a notched tip.
*Petal margin.*—Entire margin.
*Petal surface.*—Glabrous surface.
*Petal texture.*—Satiny texture.
*Bud shape.*—Tubular to oval.
*Bud dimensions.*—0.50 cm. in length by 0.50 cm. in width.
*Color of bud.*—78B.
*Calyx shape.*—Tubular with sepals fused at base.
*Calyx dimensions.*—9mm. in length and 5–6 mm. in width.
*Sepals.*—Five in number.
*Sepal shape.*—Linear.
*Sepal apex.*—Acuminate.
*Sepal color.*—Overall color is 138B with dark veins that are 86A.
*Sepal surface.*—Puberulent.
*Sepal dimensions.*—9 mm. in length and 1–1.5 mm. in width.
Reproductive organs:
*Stamen number.*—Five in number that are of unequal lengths and included.
*Stamen dimensions.*—Less than 1 mm. in width and varying from 3 mm. in length to 8 mm. in length.
*Stamen color.*—18D.
*Anthers shape and attachment.*—Oblong and basifixed.
*Anther dimensions.*—Less than 1 mm. in length and less than 1 mm. in width.
*Anther color.*—15A.
*Pollen color.*—15A.
*Quantity of pollen.*—Low to moderate amount of pollen.
*Ovary color.*—138B.
*Ovary position.*—Superior.
*Ovary shape.*—Tumescent.
*Ovary dimensions.*—1 mm. in height and 1 mm. in width.
*Pistil.*—One in number and trifid at apex.
*Pistil shape.*—Slender and filiform.
*Pistil dimensions.*—6 mm. in length and less than 1 mm. in width.
*Pistil color.*—18D.
*Stigma shape.*—Trifid.
*Stigma color.*—18A.
*Stigma dimensions.*—Less than 1 mm. in height and less than 1 mm. in width.
*Style dimensions.*—Less than 1 mm. in width and 6 mm. in length.
*Style color.*—18D.
Seed: Seed production is rarely observed in other *Phlox subulata* cultivars and has not been observed by the inventor in the present invention.
Disease resistance: Susceptible to Downy Mildew.

I claim:

1. A new and distinct cultivar of *Phlox subulata* plant named 'Bubble Gum' as described and illustrated.

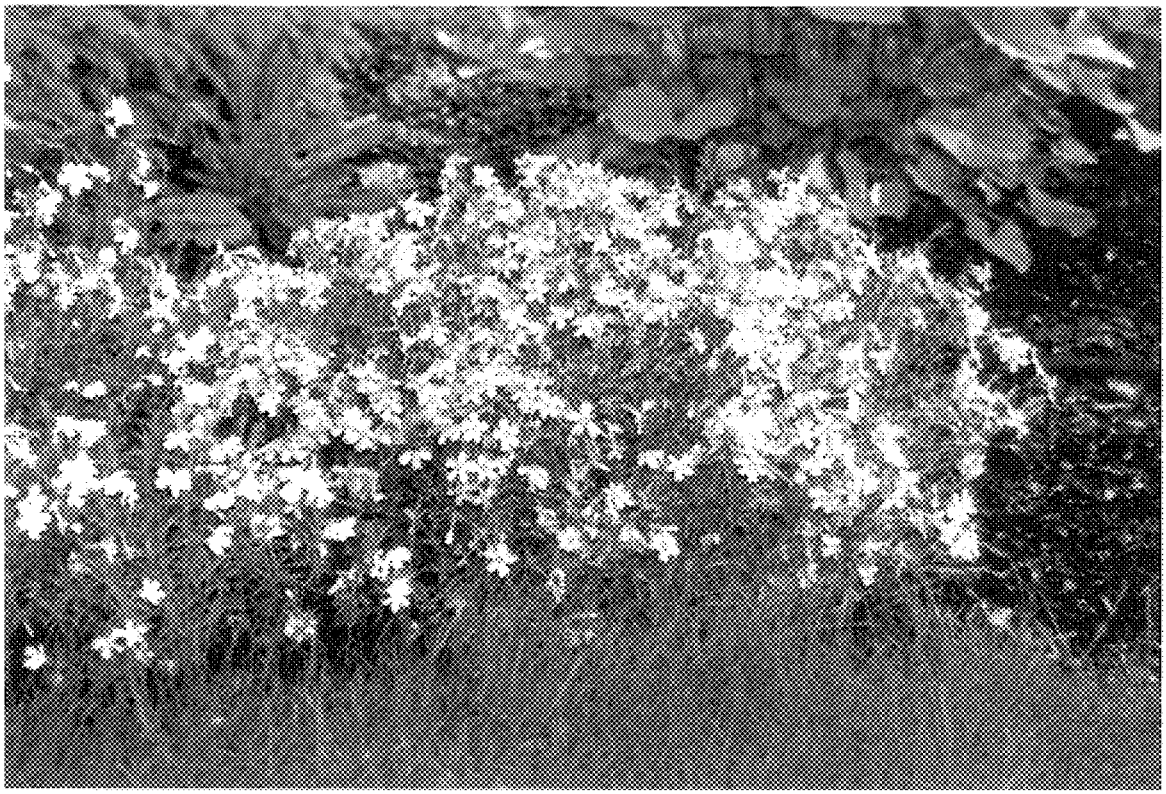

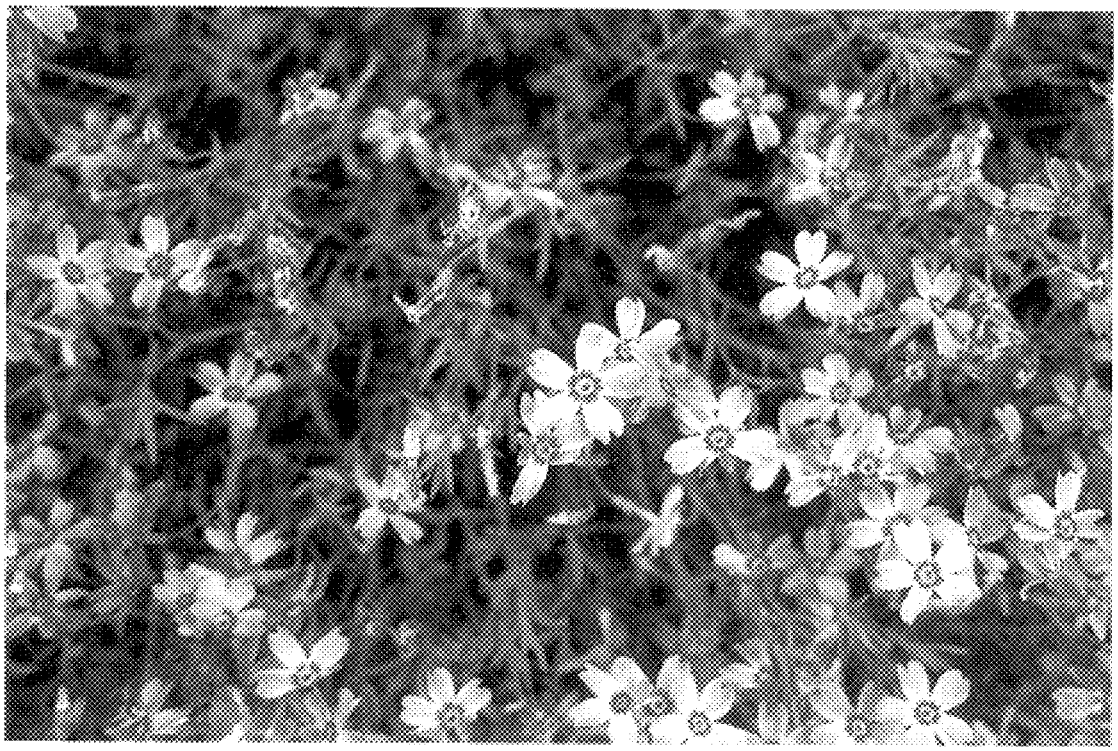

* * * * *